(12) United States Patent
Verhaert

(10) Patent No.: US 7,291,371 B2
(45) Date of Patent: Nov. 6, 2007

(54) MECHANICAL CLOSURE TAPE

(75) Inventor: Anne Verhaert, Vorselaar (BE)

(73) Assignee: Avery Dennison Corporation, Pasadena, CA (US)

( * ) Notice: Subject to any disclaimer, the term of this patent is extended or adjusted under 35 U.S.C. 154(b) by 264 days.

(21) Appl. No.: 10/775,305

(22) Filed: Feb. 10, 2004

(65) Prior Publication Data

US 2004/0170794 A1    Sep. 2, 2004

Related U.S. Application Data

(60) Provisional application No. 60/447,057, filed on Feb. 12, 2003.

(51) Int. Cl.
  B32B 33/00    (2006.01)
  B32B 3/06     (2006.01)
  A44B 18/00    (2006.01)
  A61F 13/15    (2006.01)

(52) U.S. Cl. ............... 428/40.1; 428/100; 24/306; 604/389; 604/390; 604/391

(58) Field of Classification Search ............ 428/40.1, 428/100; 24/306; 604/389–391
See application file for complete search history.

(56) References Cited

U.S. PATENT DOCUMENTS

| | | | |
|---|---|---|---|
| 3,748,701 A | 7/1973 | De Mestral | 24/204 |
| 3,833,456 A | 9/1974 | Reed et al. | 161/167 |
| 3,932,328 A | 1/1976 | Korpman | 260/27 BB |
| 4,020,842 A | 5/1977 | Richman et al. | 128/287 |
| 4,169,303 A | 10/1979 | Lemelson | 24/204 |
| 4,710,190 A | 12/1987 | Wood et al. | 604/389 |
| 4,726,971 A * | 2/1988 | Pape et al. | 428/41.9 |
| 4,795,456 A | 1/1989 | Borgers et al. | 604/390 |
| 4,869,724 A | 9/1989 | Scripps | 604/389 |
| 5,019,065 A | 5/1991 | Scripps | 604/385.1 |
| 5,053,028 A | 10/1991 | Zoia et al. | 604/385.1 |
| 5,860,964 A | 1/1999 | Willekens et al. | 604/389 |
| 5,914,165 A | 6/1999 | Freedman | 428/40.1 |
| 5,926,926 A * | 7/1999 | Kato | 24/442 |
| 6,146,369 A | 11/2000 | Hartman et al. | 604/391 |
| 6,363,587 B1 | 4/2002 | Richter et al. | 24/306 |
| 6,419,667 B1 | 7/2002 | Avalon et al. | 604/391 |
| 6,463,633 B1 | 10/2002 | Sangani et al. | 24/304 |
| 6,524,294 B1 | 2/2003 | Hilston et al. | 604/386 |
| 6,526,631 B1 * | 3/2003 | Alberg et al. | 24/306 |
| 6,669,887 B2 | 12/2003 | Hilston et al. | 264/173.15 |

* cited by examiner

*Primary Examiner*—Patricia L. Nordmeyer
(74) *Attorney, Agent, or Firm*—Renner, Otto, Boisselle & Sklar, LLP

(57) ABSTRACT

The present invention relates to a mechanical closure tape in roll form. The closure tapes are useful in the manufacture of disposable articles, particularly disposable diapers. The closure tape includes a fastening tape having a mechanical closure member and a release tape that completely covers the mechanical closure member during storage and transport of the tape and/or the disposable article.

16 Claims, 6 Drawing Sheets

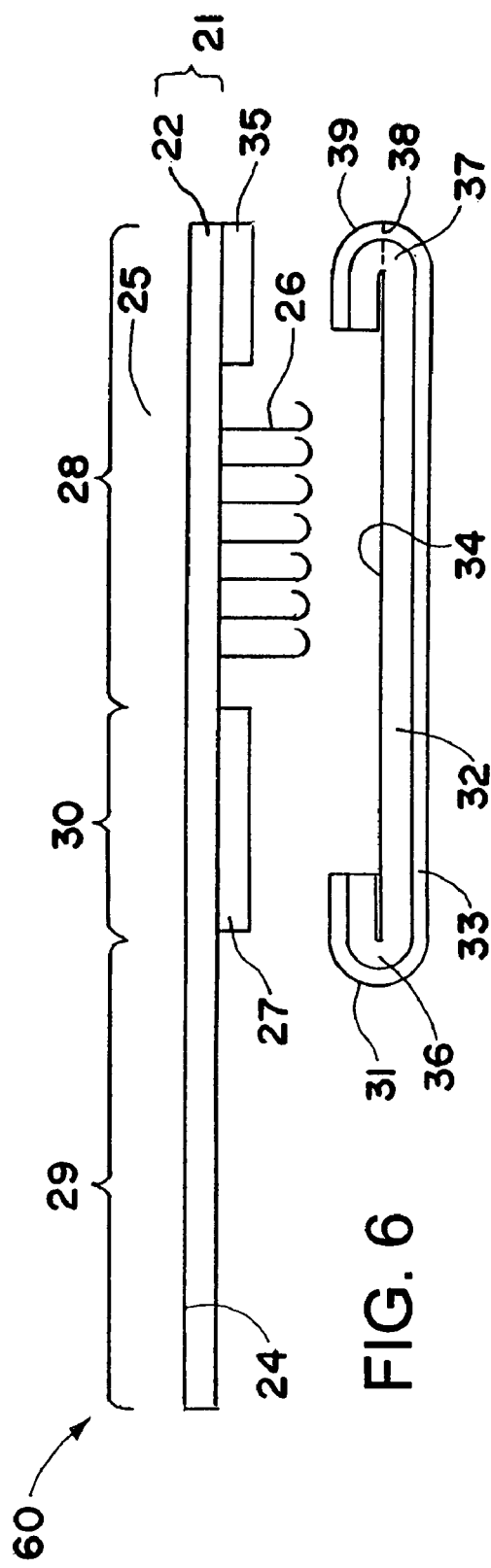
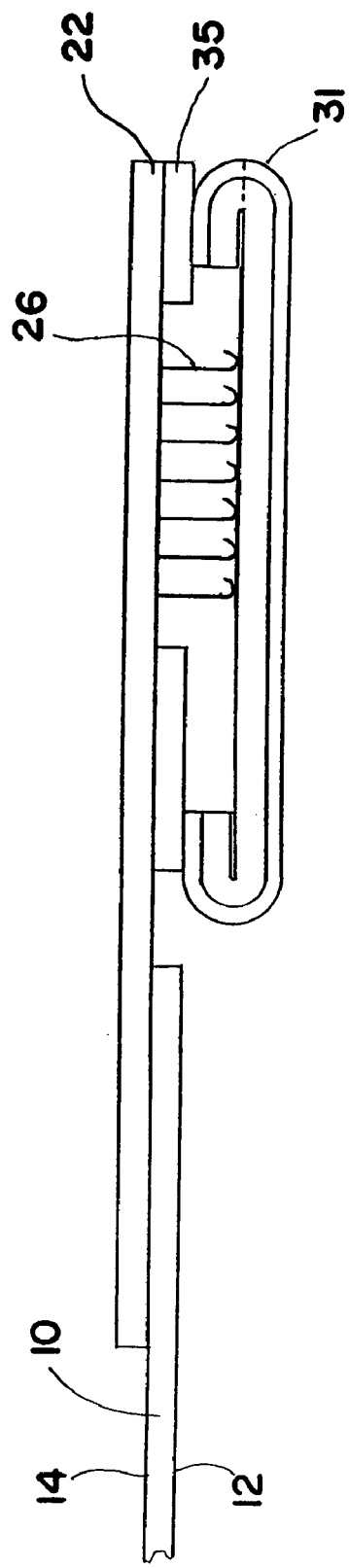
FIG. 6
FIG. 7

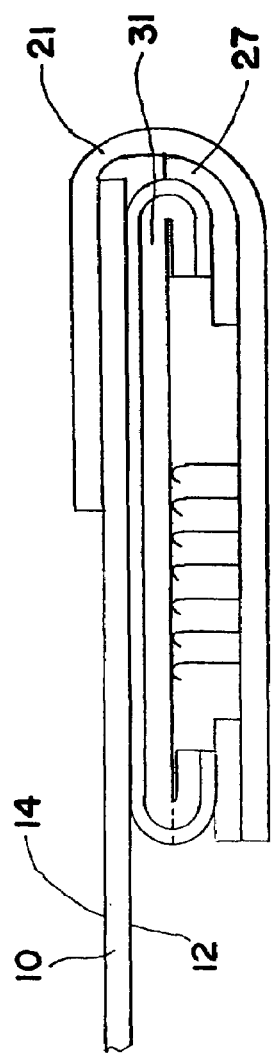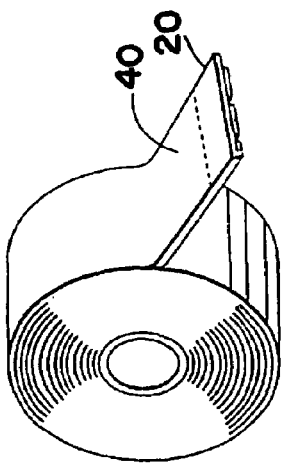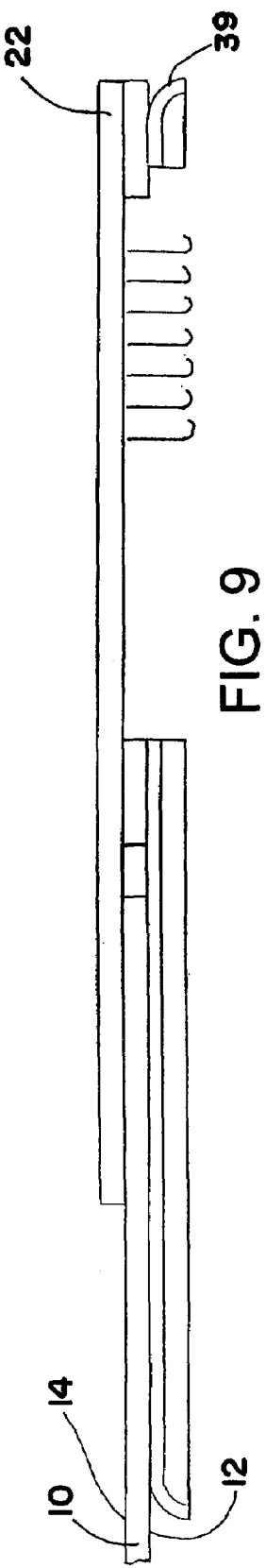
FIG. 8
FIG. 10
FIG. 9

MECHANICAL CLOSURE TAPE

This application claims the benefit of provisional application Ser. No. 60/447,057 filed on Feb. 12, 2003, which is hereby incorporated herein by reference in its entirety.

FIELD OF THE INVENTION

The present invention relates to a mechanical closure tape in roll form. The closure tapes are useful in the manufacture of disposable articles, particularly disposable diapers.

BACKGROUND OF THE INVENTION

A typical diaper construction comprises an absorbent pad or batt or the like enclosed in an outer plastic shell or a non-woven backsheet that is non-woven fabric laminated with a water impermeable layer such as a polyethylene film. A water permeable inner shell or liner is also provided to promote separation of fluid from the user.

The fastener tape system generally includes adhesive tabs fastened to one end of the diaper assembly construction at each lateral side of the diaper in a permanent "factory joint" by the diaper manufacturer using adhesives or other techniques. The tabs have a face coated with pressure sensitive adhesive. The tabs are releasably attachable to the other end of the diaper to allow unfastening to inspect the diaper followed by refastening if indicated.

The user joint may be formed by direct connection of the tab to the diaper outer surface whether the latter is formed of a plastic film or a non-woven backsheet. In the case of plastic film shells, it is typical to provide a "landing zone" of the tab to form the user joint. The landing zone may provide a plastic surface of a non-woven surface and may comprise a knit type fabric landing pad.

The fastener tape system may rely solely upon pressure sensitive adhesive in the formation of the user joint as shown in U.S. Pat. Nos. 4,795,456; 4,710,190; 4,020,842 and 3,833,456. The use of combined adhesive and mechanical fastener systems is shown in U.S. Pat. Nos. 5,019,065, 5,053,028 and 4,869,724. The teachings of all of these patents being incorporated herein by reference.

A problem often encountered with the use of mechanical fastener systems is that the mechanical fastening elements become contaminated from being in direct contact with the non-woven fabric on the diaper surface prior to use. The non-woven fibers of the diaper surface become entangled in the hooks of the mechanical fastener.

It is desirable therefore, to provide a mechanical fastening system wherein the mechanical fastening elements are protected from contamination and damage during storage and transport and prior to use of the diaper closure.

SUMMARY OF THE INVENTION

The present invention provides a composite tape in a stable roll from which a closure tab for disposable articles can be cut. In one embodiment of the invention, the composite tape comprises a backing film having a fastening surface with an adhesive layer, the backing film having a bonding extension section and an engaging extension section; a mechanical fastener material adhered to the adhesive layer of the backing film at the engaging extension section; and a release tape comprising a backing layer and an adhesive layer, wherein the backing layer of the release tape entirely covers the mechanical fastener material. The bonding extension section has exposed adhesive for attachment to a disposable absorbent article.

In another embodiment of the invention, the composite tape comprises a backing film having a fastening surface, the backing film having a bonding extension section and an engaging extension section; a mechanical fastener material adhered to the backing film at the engaging extension section; and a release tape comprising a backing layer and an adhesive layer, wherein the backing layer of the release tape entirely covers the mechanical fastener material; wherein the bonding extension section is attachable to a disposable absorbent article.

BRIEF DESCRIPTION OF THE DRAWINGS

FIG. 6 is a cross-sectional view of another embodiment of the closure tape of the invention.

FIG. 7 is a cross-sectional view of another embodiment of the closure tab of the invention when initially attached to an article.

FIG. 8 is a cross-sectional view of another embodiment the closure tab of the invention when fully attached to an article.

FIG. 9 is a cross-sectional view of another embodiment of the closure tab of the invention in a use form.

FIG. 10 is a perspective view of a closure tape roll of the invention.

DETAILED DESCRIPTION

Figure 1:
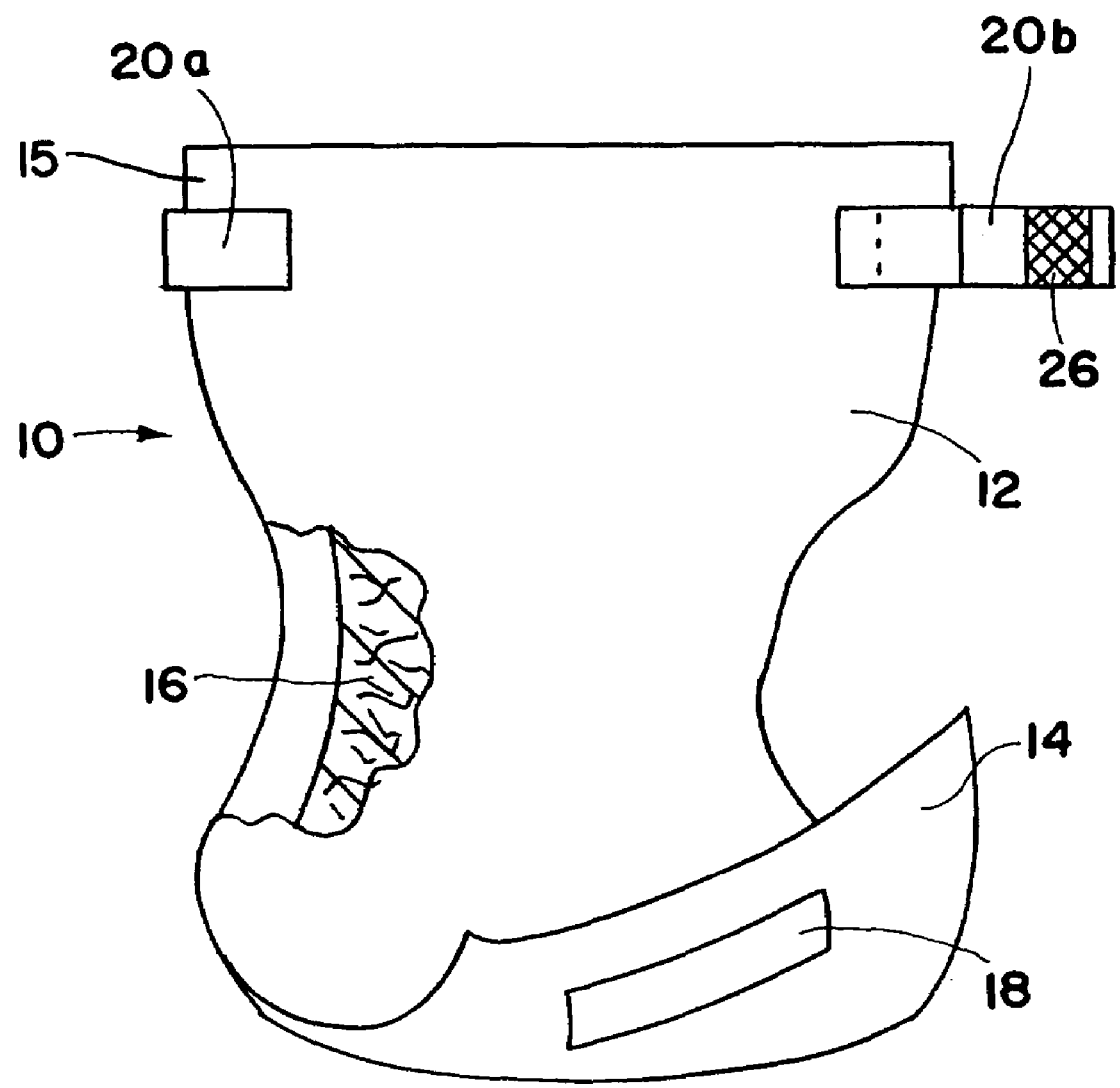
FIG. 1 is a perspective view of a disposable diaper having a tab fastener in accordance with the present invention.

Referring to FIG. 1, there is shown a disposable diaper 10 in accordance with the invention. The diaper 10 comprises a laminate or layered assembly having an inside surface 12, and an outside surface 14. Diaper 10 includes a liquid absorbent pad or batt core 16 enclosed within a liquid permeable inner shell and a liquid impermeable outer shell. The diaper 10 includes tab or tape fastener assemblies 20*a* and 20*b* secured to the end portions 15 of the diaper.

The tabs 20*a* and 20*b* are arranged to provide closure of the diaper about the wearer upon engagement with the landing area or member 18. The landing member 18 may comprise separate reinforcing tape members or a single tape piece as shown in FIG. 1. As described in further detail below, the tabs 20*a* and 20*b* may provide mechanical closure of the diaper 10.

In a first embodiment, illustrated in FIGS. 2-5, the composite tape comprises, (a) a fastening tape comprising (i) a backing film having a fastening surface, the backing film having a bonding extension section and an engaging extension section, wherein the bonding extension section attaches the fastening tape to a disposable absorbent article; (ii) an adhesive layer in contact with the fastening surface of the backing layer and (iii) mechanical fastening elements projecting from the backing film at the engaging extension section; and (b) a release tape comprising a backing layer and an adhesive layer, wherein the backing layer of the release tape entirely covers the mechanical fastening elements of the fastening tape and wherein the fastening tape is releasably attached to the release tape.

Figure 2:
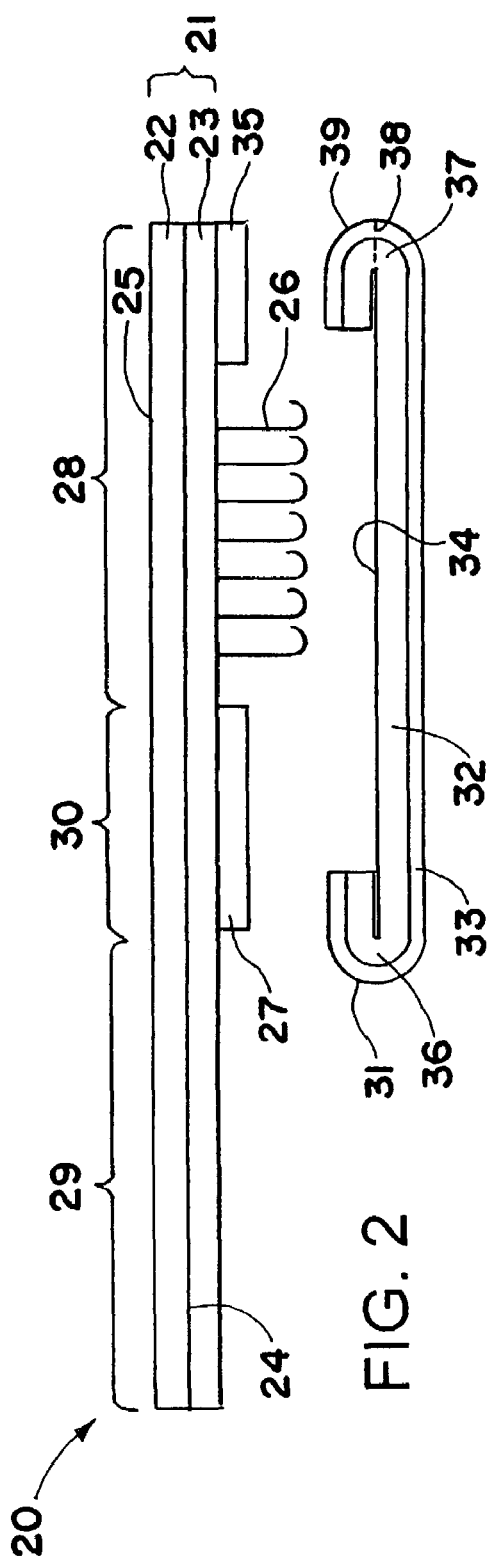
FIG. 2 is a cross-sectional view of the closure tape of the invention.

Referring to FIG. 2, the tab 20 has a composite construction. Fastening tape 21 includes a substrate or backing film 22, an adhesive layer 23 and mechanical engagement or fastening elements 26. The adhesive layer 23 is applied to the fastening surface 24 of backing film 22. Adhesive layer 23 may extend continuously along the entire backing layer 22. Alternatively, adhesive layer 23 may extend partially along backing layer 22. For example, adhesive layer 23 covers backing layer 23 in the bonding extension section 29. Fastening elements 26 are disposed on the adhesive layer 23 at the engaging extension section 28 of the backing film 22. The fastening elements 26 may be separately formed and subsequently attached to the backing layer 22 as a conventional hook and loop fabric. It is also possible to embed separate elements in the adhesive layer 23. A variety of such elements are shown in U.S. Pat. Nos. 3,748,701 and 4,169,303, the disclosures of which are hereby incorporated by reference herein. The bonding extension section 29 of the backing film 22 will be permanently bonded to the edge portion 15 of the diaper 10 in the manufacturing process by adhesive layer 23.

In a second embodiment, illustrated in FIGS. 6-9, the composite tape comprises (a) a fastening tape comprising (i) a backing film having a fastening surface, the backing film having a bonding extension section and an engaging extension section, wherein the bonding extension section attaches the fastening tape to a disposable absorbent article; and (ii) mechanical fastening elements projecting from the backing film at the engaging extension section; and (b) a release tape comprising a backing layer and an adhesive layer, wherein the backing layer of the release tape entirely covers the mechanical fastening elements of the fastening tape and wherein the fastening tape is releasably attached to the release tape.

Referring to FIG. 6, the closure tab 60 has a composite construction. Fastening tape 21 includes a substrate or backing film 22 and mechanical engagement or fastening elements 26. Fastening elements 26 are disposed on the backing film 22 at the engaging section 29 of the backing film 22. The bonding extension 29 of the backing film 22 will be permanently bonded to the edge portion 15 of the diaper 10 in the manufacturing process by any convenient manner by the diaper manufacturer, e.g., adhesive or sonic welding or other means.

The backing film 22 can be made of cloth, kraft paper, cellophane film, nonwoven webs, polymeric films or other suitable materials or laminates. The backing film may be nonextensible and formed of conventional polymers such as polypropylene, polyvinyl chloride, polyethylene terephthalate, and polyethylene film. In another embodiment, the backing film 22 is extensible. Extensible films include extensible non-woven and woven fabric and polymeric films, such as those described in U.S. Pat. No. 6,669,887, the entire disclosure of which is hereby incorporated by reference herein. A release coating is provided on the back side surface 25 of the backing film. For example, a silicone or carbamate coating may be applied to the back side surface 25 to promote deployment of the fastening tape.

Figure 11:
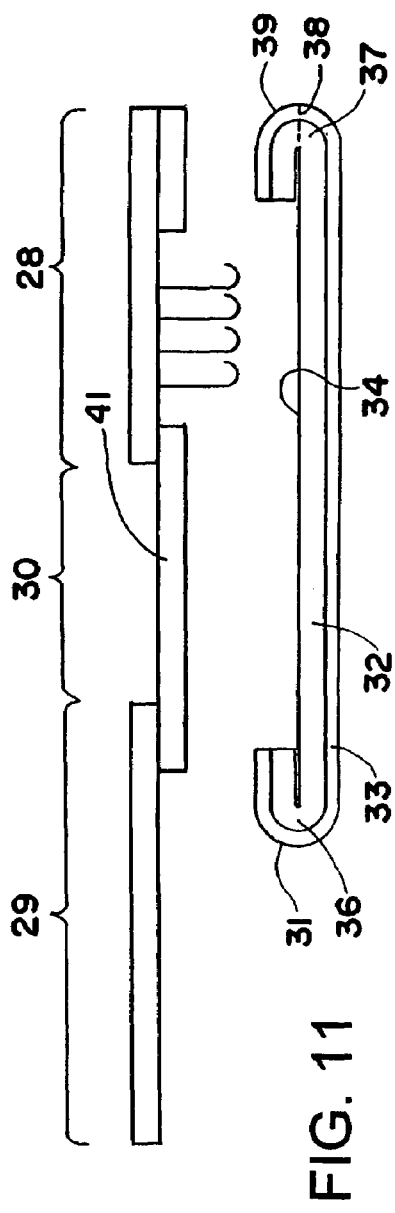
FIG. 11 is a cross-sectional view of the closure tab of the invention wherein the fastening tape includes an extensible film.

In one embodiment, backing film 22 includes an extensible intermediate section 30. Intermediate section 30 may be formed of elastomers such as the thermoplastic elastomers commercially available from Kraton Polymers under the trade designation KRATON. These elastomers may be SBS, SIS, SI, S(IS)$_x$ and SEBS block copolymers, metallocene catalyzed copolymers of ethylene with hexane, octane or other α olefins and materials such as Lycra from DuPont, and mixtures thereof. Alternatively, the intermediate section 30 may be extensible by providing a laminate construction having plurality of separation interfaces at spaced locations extending through a non-extensible portion of the laminate. This extensible film is described in U.S. Pat. No. 6,146,369, the entire disclosure of which is hereby incorporated by reference. In one embodiment, illustrated in FIG. 11, intermediate section 30 is a separate extensible film 41 attached at one end to the engaging extension 28 and at the other end to the bonding extension 29.

The adhesive layer 23 of the first embodiment is made up of an adhesive having a peel strength that is sufficient to permanently attach the backing film to the outside surface of the absorbent article and to permanently attach the mechanical fastening elements 26 to the backing film. The adhesive used may be any conventional adhesive, including pressure sensitive adhesives and non-pressure sensitive adhesives. Suitable pressure sensitive adhesives include acrylic resin and natural or synthetic based rubber adhesives. In one embodiment, the adhesive is a hot melt pressure sensitive adhesive of the A-B-A block copolymer type comprising an elastomeric B-block derived from isoprene and thermoplastic A-blocks derived from styrene as disclosed in U.S. Pat. No. 3,932,328. Illustrative rubber based adhesives include styrene-isoprene-styrene, styrene-butadiene-styrene, styrene-ethylene/butylenes-styrene and styrene-ethylene/propylene-styrene that may optionally contain diblock components such as styrene isoprene and styrene butadiene. The adhesive layer may be applied using hot-melt, solvent or emulsion techniques.

In one embodiment, the mechanical fastening elements 26 comprise any of the well known hook and loop type engagement materials as particularly exemplified by the Velcro fabric materials sold by Velcro USA or Binder hooks sold by Gottlieb Binder GmbH & Co. For example, the mechanical fastener 26 may include projecting elements or hooks. The elements may be formed of polypropylene, nylon, polyester or other relatively rigid polymer. Fastening elements 26 may be part of a two component fastening system. For example, fastening elements 26 may comprise a hook material and the landing area 18 may comprise loop elements. In another embodiment, the landing area 18 is made of the entire outer surface 14 of the diaper 10 and comprises a woven or non-woven fabric or any other suitable material that interlocks with a hook. Other known mechanical fastening structures can also be used, such as self-mating fasteners.

In one embodiment, a masking strip 27 is arranged next to fastening elements 26 in intermediate section 30 to provide a non-adhesive region. Masking strip 27 may comprise a polymeric film material, paper or a non-woven material attached to adhesive layer 23. In another embodiment, masking strip 27 comprises a detack layer to render a portion of adhesive layer 23 non-adhesive.

The engaging extension section 28 at its free end may include a finger lift 35. The finger lift 35 is provided to allow easy removal of the engaging extension section 28 from a surface from which it is attached in the storage position or to facilitate reopening. In one embodiment, the finger lift 35 comprises a thin film, for example a polypropylene film, non-woven, or paper. The thin film is attached to the fastening surface 24 at the free end of the engaging extension section 28 of the backing sheet 22. In another embodiment, the finger lift comprises an adhesive-free section of the backing sheet 22. In yet another embodiment, the finger lift comprises a folded over section of the backing sheet 22 which adhesive layer 23 applied thereto.

In one embodiment of the invention, fastening tape 21 is a stretchable tape that includes an extensible layer. Stretchable tapes are described in U.S. Pat. Nos. 6,463,633, 6,419, 667 and 6,146,369, the entire disclosures of which are hereby incorporated by reference. The stretchable tape allows greater size adjustments for a disposable diaper or garment.

As shown in FIG. 2, closure tab 20 includes fastening tape 21 and release tape 31. Fastening tape 21 includes mechanical fastening elements 26 projecting from the backing film 22. Mechanical fastening elements can be integrally formed with the backing film 22 as in the illustrated embodiment. The elements 26 extend generally perpendicular from the backing film 22. The elements 26 should be of sufficient length to provide mechanical engagement with a locking or engaging array of mechanical elements, or with a fibrous material such as a non-woven landing tape or member 18 as shown in FIG. 1 or a non-woven outer diaper surface 14. Release tape 31 completely covers mechanical fastening elements 26 during storage of the diaper. Release tape 31 is made up of backing film 32 to which adhesive layer 33 is applied. Backing film 32 may comprise any of the materials described above with reference to backing film 22. Adhesive layer 33 may comprise any of the adhesives described above with reference to adhesive layer 23. Further, a release coating may be applied to the contacting surface 34 of backing film 32. The release tape 31 is folded at each end to provide an inner fold 36 and an outer fold 37. The inner fold 36 would be adjacent the edge 15 of the diaper 10 when the closure tab is attached to the diaper 10. The outer fold 37 is provided with a weakened zone 38 that allows the release tape 31 to be broken at this point upon deployment of the tape. Generally, this line of weakness is provided by suitably cutting the release tape backing 32 intermittently along the line 38 along the width dimension of the release tape backing. The backing 32 remains continuous and attached along this line of weakness to allow the release tape to be folded and remain folded and continuous prior to use. The line of weakness could also be formed by scoring, partially cutting through backing 32, or otherwise weakening backing 32 along line 38 across substantially the entire width of the backing.

In an alternative embodiment, release tape 31 has adhered to its outer edge a peelable composite. The peelable composite comprises at least two coextruded inner layers having a peelable interface there between, each inner layer having an adhesive applied to its exterior surface. One of the adhesive layers in adhered to the outer edge of backing film 32 of the release film. The other adhesive layer is adhered to the finger lift 35. The peelable composite secures the release tape to the fastening tape to protect the mechanical fastening member during storage. When the diaper is used, the finger lift 35 is used to separate the inner layers at the peelable interface. Such peelable composites are described in U.S. Pat. No. 5,914,165, the entire disclosure of which is hereby incorporated by reference.

Figure 12:
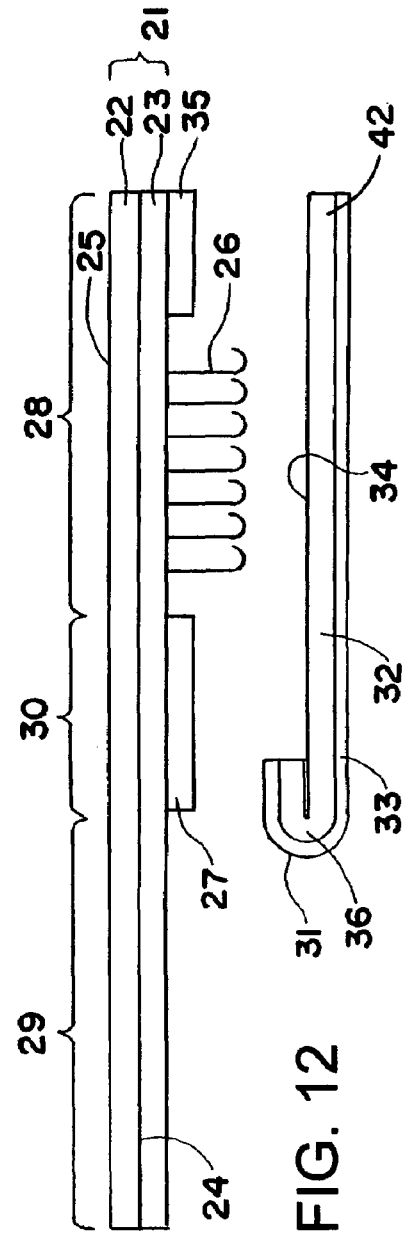
FIG. 12 is a cross-sectional view of the closure tab of the invention wherein the release tape has an unfolded edge.

In a further alternative embodiment, release tape 31 is not folded over at its outer edge 42, but is releasably attached to the fastening tape at outer edge 42 during storage and transport. This embodiment is illustrated in FIG. 12. Backing film 32 can be ultrasonically bonded to the finger lift 35. Alternatively, backing film 32 is releasably attached to finger lift 35 using adhesive, cohesive or by any other suitable means. When the diaper is used, pressure is applied to finger lift 35 to break the bond between the backing film 32 and the finger lift 35 and permit extension of the engaging extension section 28.

Release tape 31 extends from the edge portion of engaging extension section 28 of the fastening tape 21 to the intermediate section 30 of the fastening tape 21 and protects fastening member 26 from contamination and damage during storage, transport, and subsequent to being applied to the diaper before use of the diaper.

Figure 3:
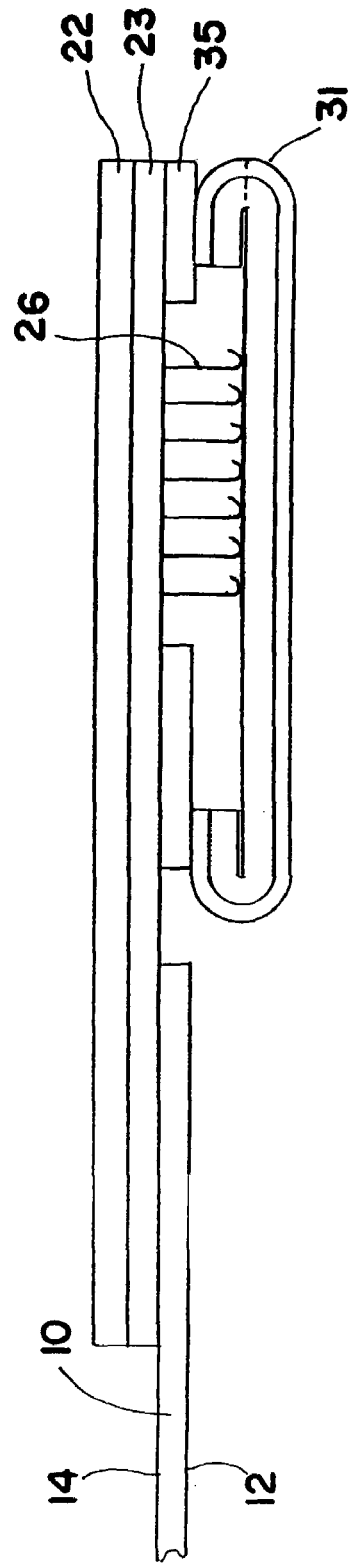
FIG. 3 is a cross-sectional view of the closure tab of the invention when initially attached to an article.
Figure 4:
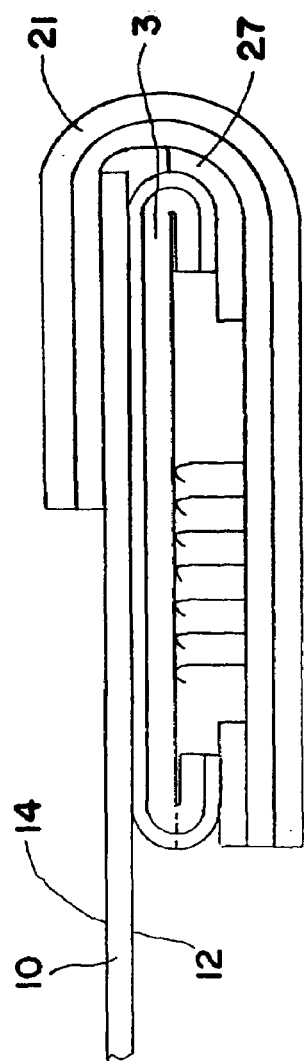
FIG. 4 is a cross-sectional view of the closure tab of the invention when fully attached to an article.
Figure 5:
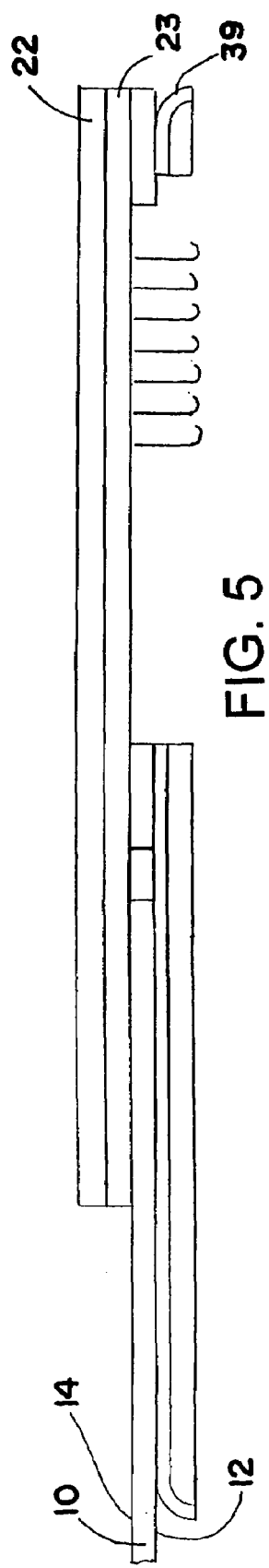
FIG. 5 is a cross-sectional view of the closure tab of the invention in a use form.

FIG. 3 depicts an intermediate step in the attachment of the closure tab 20 to the outer surface 14 of diaper 10. The completed attachment of the closure tab 20 to the diaper is shown in FIG. 4 wherein the fastening tape 21 is folded over and release tape 31 is secured to the diaper 10 in the stored position by the adhesive layer 33 to the inner surface 12 of the diaper by the adhesive layer 33. The closure tab remains in this folded condition up to the point in time that the diaper is used. Upon deployment, the engaging extension section 28 of the fastening tape 21 is extended from its folded condition at the edge of the 15 by breaking the release tab 39 along the weakened line 38. Finger lift 35 is used to initiate pulling the engaging extension section from its folded position. FIG. 5 shows the fastening member 26 exposed for use. The engaging extension section 28 comprising the fastening member 26 is then secured to the outer surface of the diaper, preferably to the landing area 18.

Similarly, for the second embodiment of FIGS. 6-9, FIG. 7 depicts an intermediate step in the attachment of the closure tab 60 to the outer surface 14 of diaper 10. The completed attachment of the closure tab 60 to the diaper is shown in FIG. 8 and FIG. 9 shows the fastening member 26 exposed for use.

The width of the roll of mechanical closure tape of the present invention depends on the intended application. Typically, the rolls that are used for closure tabs for disposable articles have a width in the range of about 30 to about 100 mm. In one embodiment, the width of the rolls is in the range of about 50 to about 70 mm. The closure tape can be provided in a roll, for example, as a disc wound roll or a spool wound roll. In order to provide a closure tape system that can be wound up to a stable roll, i.e., a roll that can be unwound continuously and at a high speed so that a closure tab can be cut therefrom without telescoping of the roll, the engaging extension section 28 occupies from about 15% to about 70% and the bonding extension section 29 occupies from about 15% to about 70% of the width of the strip.

As illustrated in FIG. 10, the closure tabs 20 and 60 of the invention can be cut from a stock roll 40. In use, a segment of the roll of composite closure tape 20 or 60 is cut from the roll in a desired length.

Although the invention has been shown and described with respect to a certain embodiment or embodiments, it is obvious that equivalent alterations and modifications will occur to others skilled in the art upon the reading and understanding of this specification. In particular regard to the various functions performed by the above described elements (components, assemblies, compositions, etc.), the terms used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A composite tape in a roll from which a closure tab for disposable articles can be cut, comprising
    a fastening tape comprising (a) a backing film having a fastening surface, the backing film having a bonding extension section and an engaging extension section, wherein the bonding extension section attaches the fastening tape to a disposable absorbent article; and (b) mechanical fastening elements projecting from the backing film at the engaging extension section; and
    a release tape comprising a backing layer and an adhesive layer, wherein the backing layer of the release tape entirely covers the mechanical fastener elements of the fastening tape and wherein the fastening tape is releasably attached to the release tape.

2. The composite tape of claim 1 wherein the fastening tape further comprises an adhesive layer in contact with the fastening surface of the backing layer.

3. The composite tape of claim 2 wherein the adhesive layer extends continuously along the entire backing layer.

4. The composite tape of claim 2 wherein the adhesive layer adheres to the bonding extension section of the backing film.

5. The composite tape of claim 1 wherein the backing film further comprises an intermediate section positioned between the bonding extension section and the engaging extension section.

6. The composite tape of claim 5 wherein the intermediate section is extensible.

7. The composite tape of claim 1 wherein at least one of the backing film and the backing layer comprises a polymeric film.

8. The composite tape of claim 7 wherein the polymeric film is nonwoven.

9. The composite tape of claim 1 wherein at least one of the backing film and backing layer comprises paper.

10. The composite tape of claim 1 wherein at least one of the backing film and the backing layer comprises an extensible composite.

11. The composite tape of claim 1 wherein at least one of the backing film and the backing layer comprises a textile.

12. The composite tape of claim 1 wherein the bonding section adhesively attaches to the disposable absorbent article.

13. The composite tape of claim 1 wherein the bonding section is welded to the disposable absorbent article.

14. The composite tape of claim 1 wherein the release tape has an outer fold and an inner fold.

15. The composite tape of claim 14 wherein the outer fold of the release tape has a plurality of perforations for releasing the fastening tape from the release tape.

16. The composite tape of claim 1 wherein the mechanical fastening elements comprise hooks.

* * * * *